(12) United States Patent
Grund

(10) Patent No.: US 12,714,208 B2
(45) Date of Patent: Aug. 25, 2026

(54) WEARABLE CALMING ACCESSORY

(71) Applicant: Janet Grund, Morningside, MD (US)

(72) Inventor: Janet Grund, Morningside, MD (US)

( * ) Notice: Subject to any disclaimer, the term of this patent is extended or adjusted under 35 U.S.C. 154(b) by 1097 days.

(21) Appl. No.: 17/849,606

(22) Filed: Jun. 25, 2022

(65) Prior Publication Data

US 2023/0413957 A1 Dec. 28, 2023

(51) Int. Cl.
*A44C 5/00* (2006.01)
*A61B 5/16* (2006.01)
*A61M 21/00* (2006.01)

(52) U.S. Cl.
CPC .......... *A44C 5/0023* (2013.01); *A44C 5/0015* (2013.01); *A61B 5/165* (2013.01); *A61M 21/00* (2013.01)

(58) Field of Classification Search
CPC ..................... A61M 21/00–02; A61B 5/16–18
See application file for complete search history.

(56) References Cited

U.S. PATENT DOCUMENTS 11,184,971 B1 * 11/2021 Rubin .................. H05B 47/198
2002/0089859 A1 * 7/2002 Jackson ............. A44C 15/0015
362/571

FOREIGN PATENT DOCUMENTS

CA 2684255 A1 * 1/2011
WO WO-2019215682 A1 * 11/2019 ............ A44C 5/003

* cited by examiner

*Primary Examiner* — Thaddeus B Cox
(74) *Attorney, Agent, or Firm* — The Iwashko Law Firm, PLLC; Lev Ivan Gabriel Iwashko

(57) ABSTRACT

A wearable calming accessory, including a main body to be disposed around at least a portion of a body of a user, the main body including a first bead to reduce stress in response to being observed by the user, a second bead connected to at least a portion of the first bead to reduce stress in response to being observed by the user, a third bead connected to at least a portion of the second bead to reduce stress in response to being observed by the user, a fourth bead connected to at least a portion of the third bead to reduce stress in response to being observed by the user, a fifth bead connected to at least a portion of the fourth bead to reduce stress in response to being observed by the user, a sixth bead connected to at least a portion of the fifth bead to reduce stress in response to being observed by the user, a seventh bead connected to at least a portion of the sixth bead to reduce stress in response to being observed by the user, and an eighth bead connected to at least a portion of the seventh bead to reduce stress in response to being observed by the user, and a connecting fastener to connect the first bead, the second bead, the third bead, the fourth bead, the fifth bead, the sixth bead, the seventh bead, and the eighth bead to each other.

3 Claims, 1 Drawing Sheet

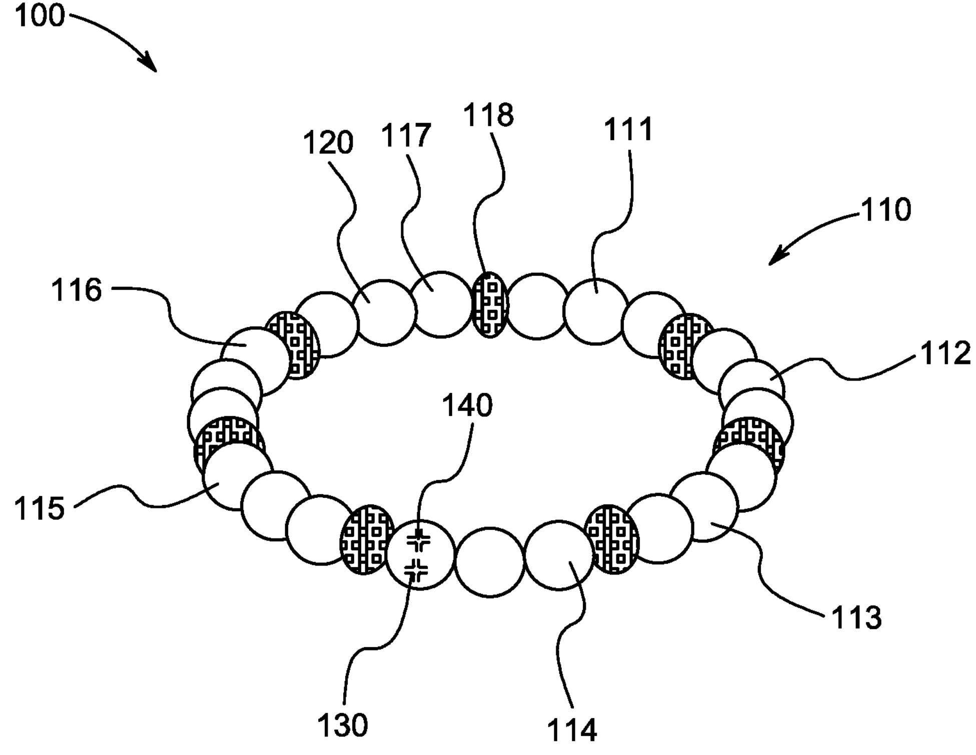
100
110
111
112
113
114
115
116
117
118
120
130
140

WEARABLE CALMING ACCESSORY

BACKGROUND

1. Field

The present general inventive concept relates generally to an accessory, and particularly, to a wearable calming accessory.

2. Description of the Related Art

Every person is presented with different challenges in the course of life. The different challenges may result in positive and/or negative thoughts and/or feelings. Negative thoughts and/or feelings can decrease productivity as well as impact a third party, such as a family member and/or a friend.

Learning how to redirect these types of thoughts and/or feelings away can be difficult to achieve without assistance, such as from a psychiatrist and/or a psychologist. Still, adopting a practice to focus on positive thoughts and/or feelings can take years to learn.

Therefore, there is a need for a wearable calming accessory that focuses a person's thoughts and feelings to reduce stress and provide mental relief while being observed by a user.

SUMMARY

The present general inventive concept provides a wearable calming accessory.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a wearable calming accessory, including a main body to be disposed around at least a portion of a body of a user, the main body including a first bead to reduce stress in response to being observed by the user, a second bead connected to at least a portion of the first bead to reduce stress in response to being observed by the user, a third bead connected to at least a portion of the second bead to reduce stress in response to being observed by the user, a fourth bead connected to at least a portion of the third bead to reduce stress in response to being observed by the user, a fifth bead connected to at least a portion of the fourth bead to reduce stress in response to being observed by the user, a sixth bead connected to at least a portion of the fifth bead to reduce stress in response to being observed by the user, a seventh bead connected to at least a portion of the sixth bead to reduce stress in response to being observed by the user, and an eighth bead connected to at least a portion of the seventh bead to reduce stress in response to being observed by the user, and a connecting fastener to connect the first bead, the second bead, the third bead, the fourth bead, the fifth bead, the sixth bead, the seventh bead, and the eighth bead to each other.

The connecting fastener may be magnetic.

The wearable calming accessory may further include a calming control unit disposed within at least a portion of at least one of the first bead, the second bead, the third bead, the fourth bead, the fifth bead, the sixth bead, the seventh bead, and the eighth bead to adjust at least one of an illumination level and a color of a light in response to determining negative thoughts of the user based on at least one of a facial orientation of the user, an expression of dissatisfaction of the user, and an eye reading of the user after scanning an eye of the user.

The calming control unit may adjust at least one of the illumination level and the color of the light in response to learning whether at least one of the illumination level and the color of the light causes a positive response based on reactions from the user.

BRIEF DESCRIPTION OF THE DRAWINGS

These and/or other features and utilities of the present generally inventive concept will become apparent and more readily appreciated from the following description of the embodiments, taken in conjunction with the accompanying drawings of which:

FIG. 1 illustrates a perspective view of a wearable calming accessory, according to an exemplary embodiment of the present general inventive concept.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

LIST OF COMPONENTS

Wearable Calming Accessory 100
Main Body 110
First Bead 111
Second Bead 112
Third Bead 113
Fourth Bead 114
Fifth Bead 115
Sixth Bead 116
Seventh Bead 117
Eighth Bead 118
Connecting Fastener 120
Calming Control Unit 130
Power Source 140

FIG. 1 illustrates a perspective view of a wearable calming accessory 100, according to an exemplary embodiment of the present general inventive concept.

The wearable calming accessory 100 may be constructed from at least one of metal, plastic, wood, glass, and rubber, etc., but is not limited thereto.

The wearable calming accessory 100 may include a main body 110, a connecting fastener 120, a calming control unit 130, and a power source 140, but is not limited thereto.

Referring to FIG. 1, the main body 110 is illustrated to be a bracelet. However, the main body 110 may be a necklace, a choker, a ring, an earring, or any other type of jewelry known to one of ordinary skill in the art, but is not limited thereto.

The main body 110 may be disposed (e.g., worn) around at least a portion of a body of a user, such as a wrist.

The main body 110 may include a first bead 111, a second bead 112, a third bead 113, a fourth bead 114, a fifth bead 115, a sixth bead 116, a seventh bead 117, and an eighth bead 118, but is not limited thereto.

The first bead 111 may include a first type of bead/gem and a first metal charm, but is not limited thereto.

The first bead 111 may be a purple agate. The first bead 111 may have a first color, such that the first bead 111 may reduce stress and/or provide mind relief to the user in response to being observed.

The second bead 112 may include a second type of bead/gem and a second metal charm, but is not limited thereto.

The second bead 112 may be connected to at least a portion of the first bead 111. The second bead 112 may be a lapis lazuli. The second bead 112 may have a second color, such that the second bead 112 may reduce stress and/or provide mind relief to the user in response to being observed.

The third bead 113 may include a third type of bead/gem and a third metal charm, but is not limited thereto.

The third bead 113 may be connected to at least a portion of the second bead 112. The third bead 113 may be a blue turquoise. The third bead 113 may have a third color, such that the third bead 113 may reduce stress and/or provide mind relief to the user in response to being observed.

The fourth bead 114 may include a fourth type of bead/gem and a fourth metal charm, but is not limited thereto.

The fourth bead 114 may be connected to at least a portion of the third bead 113. The fourth bead 114 may be a king turquoise. The fourth bead 114 may have a fourth color, such that the fourth bead 114 may reduce stress and/or provide mind relief to the user in response to being observed.

The fifth bead 115 may include a fifth type of bead/gem and a fifth metal charm, but is not limited thereto.

The fifth bead 115 may be connected to at least a portion of the fourth bead 114. The fifth bead 115 may be a tiger eye. The fifth bead 115 may have a fifth color, such that the fifth bead 115 may reduce stress and/or provide mind relief to the user in response to being observed.

The sixth bead 116 may include a sixth type of bead/gem and a sixth metal charm, but is not limited thereto.

The sixth bead 116 may be connected to at least a portion of the fifth bead 115. The sixth bead 116 may be a sefflower. The sixth bead 116 may have a sixth color, such that the sixth bead 116 may reduce stress and/or provide mind relief to the user in response to being observed.

The seventh bead 117 may include a seventh type of bead/gem and a seventh metal charm, but is not limited thereto.

The seventh bead 117 may be connected to at least a portion of the sixth bead 116. The seventh bead 117 may be an onyx. The seventh bead 117 may have a seventh color, such that the seventh bead 117 may reduce stress and/or provide mind relief to the user in response to being observed.

The eighth bead 118 may include an eighth type of bead/gem and an eighth metal charm, but is not limited thereto.

The eighth bead 118 may be connected to at least a portion of the seventh bead 117. The eighth bead 118 may be a silver space bead. The eighth bead 118 may have an eighth color, such that the eighth bead 118 may reduce stress and/or provide mind relief to the user in response to being observed.

Each of the aforementioned beads may be connected to each other in different arrangements. Moreover, the first bead 111, the second bead 112, the third bead 113, the fourth bead 114, the fifth bead 115, the sixth bead 116, the seventh bead 117, and/or the eighth bead 118 may individually and/or collectively reduce stress and/or provide mind relief to the user, such that negative thoughts and/or feelings are removed. Also, the first bead 111, the second bead 112, the third bead 113, the fourth bead 114, the fifth bead 115, the sixth bead 116, the seventh bead 117, and/or the eighth bead 118 may remind the user to associate each of the beads and/or colors with various scriptures. Additionally, there may be a plurality of each of the aforementioned beads, such as two of the first bead 111, two of the second bead 112, three of the third bead 113, etc. to create an entirety of the main body 110.

Alternatively, the first bead 111, the second bead 112, the third bead 113, the fourth bead 114, the fifth bead 115, the sixth bead 116, the seventh bead 117, and/or the eighth bead 118 may be other types of beads/gems, such as amethyst, carnelian, yellow jade, green aventurine, clear crystal, and/or red jasper.

The connecting fastener 120 may include a cord, a string, a rope, a wire, a twine, a thread, an adhesive (e.g., tape, glue), a magnet, and/or any combination thereof, but is not limited thereto.

The connecting fastener 120 may be removably connected (e.g., threaded) through the first bead 111, the second bead 112, the third bead 113, the fourth bead 114, the fifth bead 115, the sixth bead 116, the seventh bead 117, and/or the eighth bead 118. In other words, the first bead 111, the second bead 112, the third bead 113, the fourth bead 114, the fifth bead 115, the sixth bead 116, the seventh bead 117, and/or the eighth bead 118 may each have an aperture to receive the connecting fastener 120 therethrough. The connecting fastener 120 may connect the first bead 111, the second bead 112, the third bead 113, the fourth bead 114, the fifth bead 115, the sixth bead 116, the seventh bead 117, and/or the eighth bead 118 to each other.

Furthermore, the connecting fastener 120 may be a fixed size and/or elastic, such that the connecting fastener 120 may at least partially deform (e.g., bend, stretch, expand) in response to an application of force (e.g., pushing, pulling) thereto.

The calming control unit 130 may include a processing unit (e.g., a central processing unit (CPU), a microcontroller, a processor), a storage unit (e.g., a hard disk drive (HDD), a solid stated drive (SSD), a random access memory (RAM), a read-only memory (ROM)), a light, and a biometric sensor (e.g., facial recognition, iris recognition), but is not limited thereto.

The calming control unit 130 may be disposed within at least a portion of the first bead 111, the second bead 112, the third bead 113, the fourth bead 114, the fifth bead 115, the sixth bead 116, the seventh bead 117, and/or the eighth bead 118. Also, each of the first bead 111, the second bead 112, the third bead 113, the fourth bead 114, the fifth bead 115, the sixth bead 116, the seventh bead 117, and/or the eighth bead 118 may have a calming control unit 130 disposed therein. The calming control unit 130 may detect a facial orientation of the user (e.g., a frown, a scowl), an expression of dissatisfaction of the user (e.g., anger, sadness, depression, stress), and/or an eye reading of the user (e.g., intraocular eye pressure, eye movement) using the sensor and compare the facial orientation, the expression of dissatisfaction, and/or the eye reading to a predetermined standard of dissatisfaction using a program running on the calming control unit 130. In other words, the calming control unit 130 may run the program having a database of facial features, expressions, and/or intraocular eye pressure associated with negative thoughts, feelings, and/or stress of the user.

As such, the calming control unit 130 may adjust an illumination level (e.g., brightness) and/or a color of the light within the first bead 111, the second bead 112, the third bead 113, the fourth bead 114, the fifth bead 115, the sixth bead 116, the seventh bead 117, and/or the eighth bead 118 to facilitate positive thoughts and/or feelings from the user.

The calming control unit 130 may learn and/or adjust the response based on reactions from the user whether the illumination level and/or the color of the light causes a positive response.

The power source 140 may include a battery and a solar cell, but is not limited thereto.

The power source 140 may be disposed in each of the first bead 111, the second bead 112, the third bead 113, the fourth bead 114, the fifth bead 115, the sixth bead 116, the seventh bead 117, and/or the eighth bead 118. The power source 140 may be connected to the calming control unit 130 to provide power to the calming control unit 130.

Therefore, the wearable calming accessory 100 may reduce stress of the user and provide comfort. Also, the wearable calming accessory 100 may provide a channeling medium during prayer.

The present general inventive concept may include a wearable calming accessory 100, including a main body 110 to be disposed around at least a portion of a body of a user, the main body 110 including a first bead 111 to reduce stress in response to being observed by the user, a second bead 112 connected to at least a portion of the first bead 111 to reduce stress in response to being observed by the user, a third bead 113 connected to at least a portion of the second bead 112 to reduce stress in response to being observed by the user, a fourth bead 114 connected to at least a portion of the third bead 113 to reduce stress in response to being observed by the user, a fifth bead 115 connected to at least a portion of the fourth bead 114 to reduce stress in response to being observed by the user, a sixth bead 116 connected to at least a portion of the fifth bead 115 to reduce stress in response to being observed by the user, a seventh bead 117 connected to at least a portion of the sixth bead 116 to reduce stress in response to being observed by the user, and an eighth bead 118 connected to at least a portion of the seventh bead 117 to reduce stress in response to being observed by the user, and a connecting fastener 120 to connect the first bead 111, the second bead 112, the third bead 113, the fourth bead 114, the fifth bead 115, the sixth bead 116, the seventh bead 117, and the eighth bead 118 to each other.

The connecting fastener 120 may be magnetic.

The wearable calming accessory 100 may further include a calming control unit 130 disposed within at least a portion of at least one of the first bead 111, the second bead 112, the third bead 113, the fourth bead 114, the fifth bead 115, the sixth bead 116, the seventh bead 117, and the eighth bead 118 to adjust at least one of an illumination level and a color of a light in response to determining negative thoughts of the user based on at least one of a facial orientation of the user, an expression of dissatisfaction of the user, and an eye reading of the user after scanning an eye of the user.

The calming control unit 130 may adjust at least one of the illumination level and the color of the light in response to learning whether at least one of the illumination level and the color of the light causes a positive response based on reactions from the user.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A wearable calming accessory, comprising:
- a main body to be disposed around at least a portion of a body of a user, the main body comprising:
  - a first bead to reduce stress in response to being observed by the user,
  - a second bead connected to at least a portion of the first bead to reduce stress in response to being observed by the user,
  - a third bead connected to at least a portion of the second bead to reduce stress in response to being observed by the user,
  - a fourth bead connected to at least a portion of the third bead to reduce stress in response to being observed by the user,
  - a fifth bead connected to at least a portion of the fourth bead to reduce stress in response to being observed by the user,
  - a sixth bead connected to at least a portion of the fifth bead to reduce stress in response to being observed by the user,
  - a seventh bead connected to at least a portion of the sixth bead to reduce stress in response to being observed by the user, and an eighth bead connected to at least a portion of the seventh bead to reduce stress in response to being observed by the user;

a connecting fastener to connect the first bead, the second bead, the third bead, the fourth bead, the fifth bead, the sixth bead, the seventh bead, and the eighth bead to each other; and a calming control unit disposed within at least a portion of at least one of the first bead, the second bead, the third bead, the fourth bead, the fifth bead, the sixth bead, the seventh bead, and the eighth bead to adjust at least one of an illumination level and a color of a light in response to determining negative thoughts of the user based on at least one of a facial orientation of the user, an expression of dissatisfaction of the user, and an eye reading of the user after scanning an eye of the user.

2. The wearable calming accessory of claim 1, wherein the connecting fastener is magnetic.

3. The wearable calming accessory of claim 1, wherein the calming control unit adjusts at least one of the illumination level and the color of the light in response to learning whether at least one of the illumination level and the color of the light causes a positive response based on reactions from the user.

* * * * *